(12) United States Patent
Kröner et al.

(10) Patent No.: US 7,010,085 B2
(45) Date of Patent: Mar. 7, 2006

(54) TOMOGRAPHY IMAGING SYSTEM WITH AN ACQUISITION UNIT AND A PATIENT POSITIONING TABLE WITH A HORIZONTALLY MOVABLE PATIENT BOARD

(75) Inventors: Hans-Jürgen Kröner, Baiersdorf (DE); Michael Loser, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 7 days.

(21) Appl. No.: 10/798,668

(22) Filed: Mar. 11, 2004

(65) Prior Publication Data

US 2004/0223584 A1 Nov. 11, 2004

(30) Foreign Application Priority Data

Mar. 14, 2003 (DE) ................... 103 11 309

(51) Int. Cl.
*A61B 6/04* (2006.01)
(52) U.S. Cl. .......................... 378/20; 378/208
(58) Field of Classification Search .................... 378/4, 378/196, 195, 190, 208, 209, 20, 50; 600/407, 600/427, 424, 414, 415; 5/601, 81.1 HS
See application file for complete search history.

(56) References Cited

U.S. PATENT DOCUMENTS

| | | | |
|---|---|---|---|
| 4,131,802 A | * | 12/1978 | Braden et al. ................. 378/20 |
| 4,177,382 A | * | 12/1979 | Hounsfield ..................... 378/4 |
| 6,459,923 B1 | * | 10/2002 | Plewes et al. .............. 600/411 |
| 6,668,403 B1 | | 12/2003 | Seufert |
| 6,810,103 B1 | * | 10/2004 | Tybinkowski et al. ......... 378/4 |
| 2002/0104163 A1 | | 8/2002 | Reimann |
| 2002/0112288 A1 | | 8/2002 | Seufert |

OTHER PUBLICATIONS

H. Morneburg, *Bildgebende Systeme Für die medizinsche Diagnostik*, ISBN 3-89578-002-0 (1995), pp. 429-466.
W. Kalender, *Computermographie*, ISBN 3-89578-082-0 (2000), pp. 17-34.

* cited by examiner

*Primary Examiner*—David V. Bruce
*Assistant Examiner*—Hoon Song
(74) *Attorney, Agent, or Firm*—Schiff Hardin LLP

(57) ABSTRACT

A tomography imaging system, preferably a CT device, includes at least one acquisition unit and a patient positioning table with a horizontally movable board, which can be slid through the scanning region of the acquisition unit for examination. The imaging system includes at least one first support device, which supports the patient board after passing through the scan region, which support device is directly attached to the acquisition unit on a side of the unit opposite the side facing the patient positioning table. The system can include a second support device, which is mounted on the patient positioning table for supporting the patient board before it enters the scan region of the acquisition unit.

16 Claims, 2 Drawing Sheets

TOMOGRAPHY IMAGING SYSTEM WITH AN ACQUISITION UNIT AND A PATIENT POSITIONING TABLE WITH A HORIZONTALLY MOVABLE PATIENT BOARD

BACKGROUND OF THE INVENTION

The present invention is concerned with a tomography imaging system, preferably a CT device, which comprises an acquisition unit, a patient positioning table with a horizontally movable patient board or plate, which patient board can be slid through a scan region of the acquisition unit for examination, and a first support device which is arranged with regard to the patient positioning table to support the patient board upon passing through the scan region.

Technology of tomography imaging systems, in particular of computer tomography devices, is generally known. These are described in portions of books by H. Morneburg, "Bildgebende Systeme für die medizinsche Diagnostik", ISBN 3-89578-002-0 (1995), pp. 429–466 and by W. Kalender, "Computertomographie", ISBN 3-89578-082-0 (2000), pp. 17–34.

Patient positioning systems used in connection with tomography imaging systems are known in the patent literature, for example, see U.S. Pat. No. 6,668,403 B2, whose disclosure is incorporated herein by reference thereto, and U.S. Patent Application Publication No. US 2002/0104163 A1, whose disclosure is incorporated herein by reference thereto, and which claims priority from German 101 03 331.1. In this printed application, a tomography imaging system is disclosed with a patient positioning table with a horizontally movable patient board or plate, which, for additional support of the extending patient board, has, on the side of the acquisition unit opposite the patient positioning table, an additional (as the case may be) height-adjustable support that is positioned separately from the acquisition unit and that should support the patient board in the extended state.

Because of the support of the patient board with the height-adjustable support, it is now possible to move along the scan path or even provide a full-body or whole-body scan.

A disadvantage with this known tomography imaging system is that the height-adjustable support should be arranged at a sufficient distance from the acquisition unit in order to not prevent the tilting of the acquisition unit before or between the scans. However, if the distance of the height-adjustable support to the acquisition unit is selected too large, the range in which the patient board is not supported is also too large. A deflection or warpage of the patient board will occur given an incumbent patient. The deflection of the patient board and the imprecise patient position will result and have a negative influence on the measurements. It would namely be conceivable to prevent the deflections of the patient board by increasing the rigidity of the board, for example by use of stiffening materials; however, the material absorption behavior given the use of additional material also negatively affects the measurements of the device.

The known tomography imaging system is moreover not particularly comfortable with regard to the positioning of the patient. The patient to be examined should always be inserted into the opening of the acquisition unit in the same position in order to ensure the reproducibility of the examination results and the exactitude of the image representation. For this, a certain positioning effort is necessary in the known tomography imaging system. The patient board must be aligned with regard to the acquisition unit and, at the same time, the height-adjustable support must be moved so that the patient board is not tilted upward or downward. There are, thus, three units to be positioned, namely the patient board with the patient, the acquisition unit and the height-adjustable support.

Another disadvantage of this known tomography imaging system exists in the additional space requirement for the height-adjustable support. There is, thus, a space requirement on one side of the acquisition unit for the positioning device for the patient positioning table with a horizontally movable patient board and on the other side of the acquisition unit, additional space is necessary for the height-adjustable support. Overall, the measurement arrangement of the tomography imaging system with the necessary peripheral devices is very long along the movement direction of the patient board, so that a correspondingly large measurement space must also be available.

SUMMARY OF THE INVENTION

It is an object of the invention to provide a tomography imaging system, preferably a computer tomography device, which comprises at least one acquisition unit and a patient positioning table with a horizontally movable patient board, which patient board can be slid through the scan region of the acquisition unit during the examination, which table enables an optimally long movement path of the patient board and, thus, a large scan region, and at the same time, is implemented short and compact in the direction of this movement path.

Another object is to provide a tomography imaging system comprising an acquisition unit, a patient positioning table with a horizontally movable patient board, which patient board can be slid through a scan region of the acquisition unit for examination, and a first support device, which is arranged with regard to the patient positioning table and which supports the patient board upon passing through the scan region.

These objects are achieved by a tomography imaging system, preferably a CT device, which has at least one acquisition unit and a patient positioning table with a horizontally movable patient board, which patient board can be slid through a scan region of the acquisition unit for examination, and a support for the movable patient board that enables the tomography imaging system to be implemented very compactly, the effort in the positioning of the patient to be reduced and the acquisition unit to be tilted unhindered.

Corresponding to this realization, the present invention provides an improved tomography imaging system, preferably a CT device, with at least one acquisition unit and a patient positioning table with a horizontally movable patient board, which patient board can be slid through a scan region of the acquisition unit for examination, to the effect that the first support is directly attached to the acquisition unit.

In that the first support device is directly attached to the acquisition unit, the "unsupported region" of the patient board can be substantially shortened in comparison to the previously-known height-adjustable support. The deflection of the patient board, which has a negative influence on the exact image representation, is significantly reduced.

Furthermore, the entire arrangement of the tomography imaging system can be fashioned more compactly, since the space that was previously provided for the height-adjustable support is eliminated. In addition, with a close attachment of the first support device to the acquisition unit, the support device can be particularly well adapted to the housing form of the acquisition unit and to the corresponding boundary surfaces given a tilting of the acquisition unit, so that the freedom of movement of the acquisition unit upon tilting is not limited by the support device.

The new tomography imaging system also appears to be advantageous with regard to the positioning of the patient. The positioning of the height-adjustable support does not apply. The acquisition unit and the support device form one unit via the direct arrangement, so that only the patient board is to be positioned with regard to this unit.

According to the invention, the first support device is directly attached to the acquisition unit. The "unsupported region" of the patient board can thereby be particularly shortened, since the patient board is supported within the opening of the acquisition unit. If, for example, it is used in a magnetic resonance apparatus, this first support device can also comprise materials that are not ferro-, para-, or diamagnetic, in order that the magnetic field is not influenced by this support.

Given tilting of the acquisition unit, the separation from the housing of the acquisition unit to the patient board can vary. It is, therefore, advantageous when the first support device is constructed so that it can be extended. The contact of the first support device to the patient board can be automatically maintained and, thus, the horizontal position of the patient board can be stabilized. For example, an electrical, hydraulic or pneumatic movement mechanism can be used for changing the position of the contact of the first support device.

It is advantageous when a control means is directly provided for the first support device which regulates the extension length of the first support device, so that an automatic adjustment of the extension length in order to hold the patient board in a horizontal position occurs given a tilting event of the acquisition device. On the one hand, via the maintenance of the horizontal position of the patient board, it prevents the position of the patient on the patient board from changing and, thus, the image representation from deteriorating during the scan. On the other hand, jerking movements of the patient board, which may alarm the patient during the measurement, can be prevented. Such a control means can be realized with the aid of a distance determining laser that determines the precise distance of the patient board from the floor region and from the first support device without contacting the board.

A particularly stable support of the patient board can be achieved when, in the new tomography imaging system, a second support device is mounted to be extendable, preferably in the horizontal direction. A support of the patient board at three points, which include the patient positioning table and both support devices, is thereby achieved. It would be possible to save material on the patient board without simultaneously increasing the deflection of the board. The material savings on the patient board means that less foreign material which interferes with the measurements is introduced into the scan region of the acquisition unit.

It is advantageous in the implementation of the first and/or second support device when rotary elements or members, such as rollers or wheels, are attached in the contact region with the patient board. The movement of the patient board in and out of the scan region can thereby occur without jolts. A homogenous movement of the patient board assists the comfort of the incumbent patient and, at the same time, the quality of the acquired image.

In another embodiment, the first and/or second support devices are equipped with runners in the contact region with the patient board. Complementary rotary members, such as rollers or wheels, are mounted on the patient board or bed at the contact region at which runners engage. The rollers or wheels can comprise rubberized or inflated tires and can be attached to the patient board with the aid of an elastic or spring-like bearing. The impacts can thereby be absorbed at the point in time of the contact with the runners of the support device and during the movement of the patient board.

So that the patient board can be optimally moved free of shock or jars, it can be sensible to provide a first and/or second support device with damping elements, preferably gas compression springs. Such damping elements can be formed of materials that are suitable with regard to the permeability number and the permittivity number in order to not interfere with the magnetic and electrical fields. Additionally or alternatively, damping elements can also be arranged in the contact region on the patient board. Such damping elements can, for example, be realized as plastic plates that are attached to the patient board by means of foam mats.

Other advantages and features of the invention will be readily apparent from the following description of the preferred embodiments, the drawings and claims.

DESCRIPTION OF THE PREFERRED EMBODIMENTS

Figure 1:
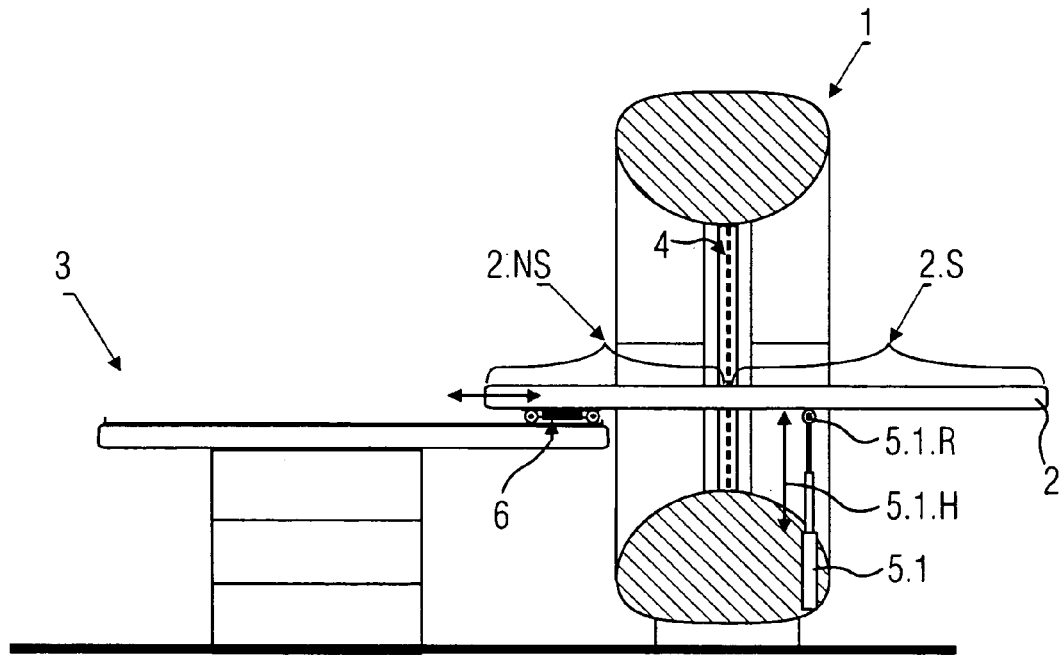
FIG. 1 is a side elevational view, with portions broken away for purposes of illustration, of a tomography imaging system with a support device which is directly attached to the acquisition unit of the imaging system.
Figure 2:
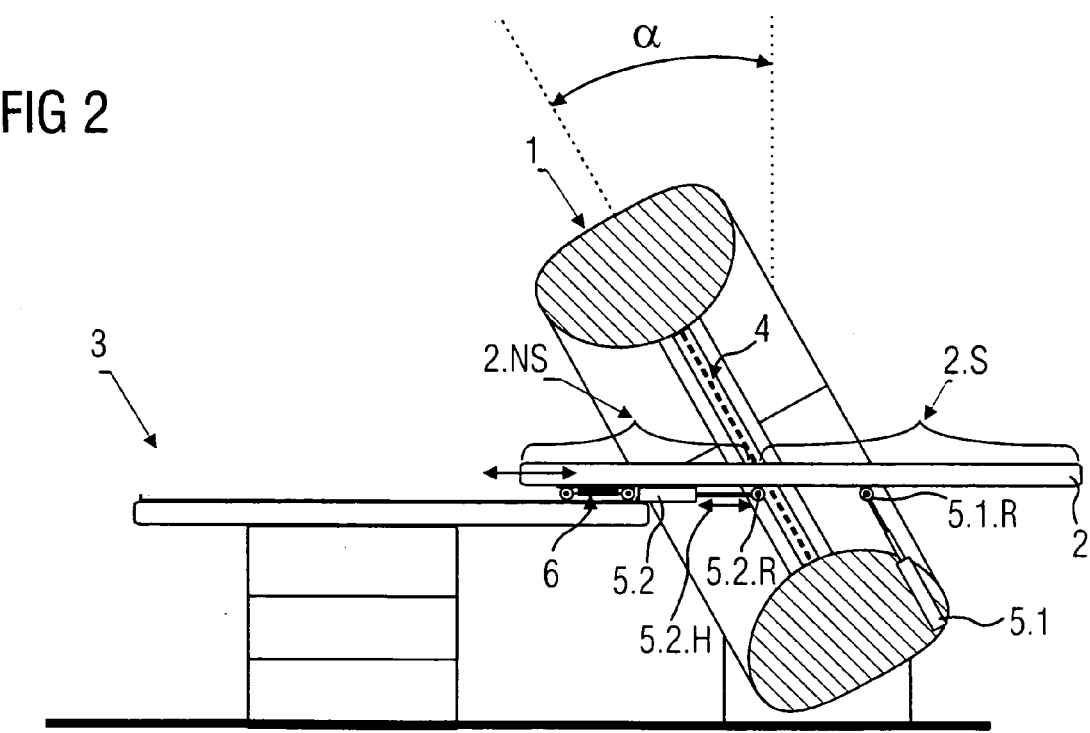
FIG. 2 is a side elevational view, with portions broken away for purposes of illustration, of a tomography imaging system similar to FIG. 1 with the additional second support device on the patient positioning table and with a tilted acquisition unit.

The principles of the present invention are particularly useful when incorporated in a tomography imaging system illustrated in FIG. 1 as a side view. The system includes a measuring region called an acquisition unit 1 or a gantry, which has an opening through which the patient is passed. As illustrated, the acquisition unit 1 has a scan region 4 which is illustrated in dashed lines. The acquisition unit can scan in various planes and can, therefore, be tilted, as illustrated in FIG. 2, from the upright position shown in FIG. 1. For a tomographical examination, the subject to be examined, for example a body section or the entire body of an animal or a person, must pass through this scan region 4.

A patient positioning table 3 is shown in the left region of FIG. 1. This patient positioning table 3 possesses, in the upper region, a horizontally movable patient board or plate 2, on which, for example, a human or an animal patient can be placed. The subject to be examined is situated on the patient board 2, which board can be driven into and out of the scan region 4 that is located within the acquisition unit with the aid of a movement mechanism 6. The region of the patient board 2 that can pass through the scan region is designated as a maximum usable scan length 2.S. A region of the patient board that cannot pass the scan region 4 also exists, and this region is designated in FIG. 1 with 2.NS.

The patient board 2 should be sufficiently supported in order to minimize deflections due to the incumbent patient and longer scan lengths. Such deflections interfere with the exact positioning of the patient and with an exact, reproducible image representation.

To minimize the patient board deflection, the acquisition unit 1 is provided with a first support device 5.1, which is attached to the acquisition unit 1 on a side opposite or facing away from the patient positioning table 3. This first support device 5.1 comprises a telescopically extendable pressure cylinder having a roller 5.1.R attached to the upper end of the telescopic arm. This roller 5.1.R contacts the patient board 2 and ensures a jolt-free movement of the patient board 2. The patient board 2 is, thus, on the one hand, supported by the movement of the mechanism 6 of the patient positioning table 3 and, on the other hand, by the roller 5.1.R of the first support device 5.1. A smaller separation of the support points of the patient board 2 results via this particular arrangement of the support device, so that a deflection of the patient board 2, which will be proportional to the square of the separation of the support points, is significantly reduced.

Additionally, shown in FIG. 1 is the movement range of the first support device 5.1, which movement is indicated by the double-arrow 5.1.H. The movement range 5.1.H corresponds to the separation of the roller 5.1.R from the pushed-together state of the telescope arm up to a point at which the patient board 2 is held level.

In FIG. 2, a side view of the tomography imaging system of FIG. 1 is shown with an additional second support device 5.2. In contrast to FIG. 1, the acquisition unit 1 is additionally tilted by an angle α in the direction of the patient positioning table 3.

The second support device 5.2 is attached to the patient positioning table 3 below the patient board 2. The second support device 5.2 also includes a telescopically extendable pressure cylinder which ends with a roller 5.2.R on the outer end of the telescopic arm. This roller 5.2.R contacts the patient board 2 and ensures a jolt-free movement of the patient board. The patient board is thus in total supported by three support points. The roller 5.2.R can be actively retracted via the pressure cylinder.

As an alternative to this, it is possible for the roller 5.2.R to be carried along in the movement of the patient board 2. In a particularly simple embodiment, this can, for example, be realized via a hook or a handle on the patient board 2 that engages on the roller 5.2.R upon movement of the patient board 2 into and out of the acquisition unit 1 and, thus, travels with the roller 5.2.R.

Figure 3:
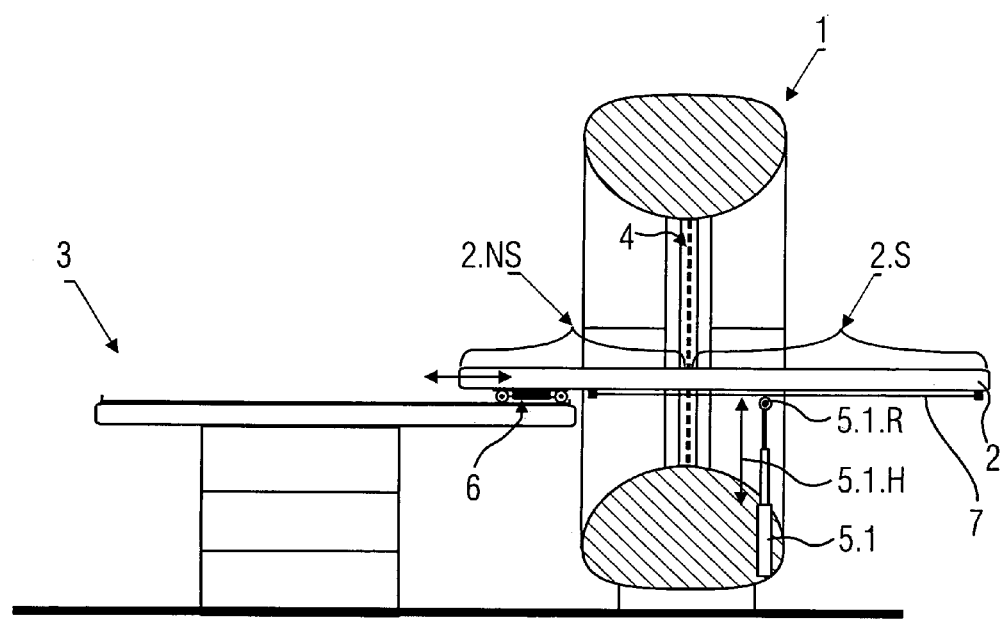
FIG. 3 is a side elevational view, with portions broken away for purposes of illustration, of a further embodiment of a tomography imaging system with a support device riding on a runner below the patient bed.

In the embodiment shown in FIG. 3, the roller 5.1R rides on a runner 7 mounted under the patient bed 2, in the contact region of the roller 5.1R.

It is understood that the preceding cited features of the invention are usable, not only in the respective specified combination, but rather also in other combinations alone or without the framework of the invention.

Overall, the invention provides a tomography imaging system which comprises a novel support device of the patient board. This support device is directly mounted in the region of the opening of the acquisition unit opposite the patient positioning table and additionally on the patient positioning table.

Although various minor modifications may be suggested by those versed in the art, it should be understood that we wish to embody within the scope of the patent granted hereon all such modifications as reasonably and properly come within the scope of our contribution to the art.

We claim:

1. A tomography imaging system comprising an acquisition unit having a gantry, a patient positioning table with a horizontally movable patient board, said patient board being slidable through a scan region of the gantry of the acquisition unit for examination, and an extendable first support device disposed to support the patient board upon passing through the scan region, said first support device being directly attached to the gantry of the acquisition unit to move therewith to extend dependent on movement of the gantry.

2. A tomography imaging system according to claim 1, which includes a second support device that is extendable in a horizontal direction and is mounted on the patient positioning table.

3. A tomography imaging system according to claim 2, wherein at least one of the first and second support devices includes a rotary member in a contact region with the patient board.

4. A tomography imaging system according to claim 2, wherein at least one of the first and second support devices includes runners in a contact region with the patient board, and complementary rotary members being mounted on the patient board engaging the runners.

5. A tomography imaging system according to claim 2, wherein at least one of the first and second support devices includes dampening elements.

6. A tomography imaging system according to claim 1, wherein a contact region of the patient board includes dampening elements.

7. A tomography imaging system according to claim 1, wherein the first support device has a rotary member for engaging a contact region of the patient board.

8. A tomography imaging system according to claim 1, wherein the first support device includes a runner in a contact region with the patient board and complementary rotary members being mounted on the patient board to engage the runners.

9. A tomography imaging system according to claim 1, wherein the first support device comprises damping elements.

10. A tomography imaging system comprising an acquisition unit, a patient positioning table with a horizontally movable patient board, which patient board being slidable through a scan region of the acquisition unit for examination, a first support device being arranged with regard to the patient positioning table, said support device supporting the patient board upon passing through the scan region said first support device being directly attached to the acquisition unit and being extendable, and control means being directly provided for the first support device which regulates an extension length of the first support device, so that an automatic compensation of the extension length automatically occurs given a tilting of the acquisition unit in order to keep the patient board in a horizontal position.

11. A tomography imaging system according to claim 10, which includes a second support device that is extendable substantially in the horizontal direction and is mounted on the patient positioning table.

12. A tomography imaging system according to claim 11, wherein at least one of the first and second support devices includes a rotary member in a contact region with the patient board.

13. A tomography imaging system according to claim 2, wherein at least one of the first and second support devices includes runners in contact with the region of the patient board, whereby complementary rotary members are mounted on the patient board.

14. A tomography imaging system according to claim 13, wherein one of the first and second support devices includes dampening elements.

15. A tomography imaging system according to claim 14, wherein the dampening elements are gas compression springs.

16. A tomography imaging system according to claim 13, wherein the contact region comprises dampening elements.

* * * * *